United States Patent
Peterson et al.

(10) Patent No.: US 8,658,655 B2
(45) Date of Patent: Feb. 25, 2014

(54) INHIBITION OF ACTIVATED CDC42-ASSOCIATED KINASE 1

(75) Inventors: Jeffrey R. Peterson, Cheltenham, PA (US); Haiching Ma, Malvern, PA (US); Sean Deacon, Philadelphia, PA (US)

(73) Assignees: Fox Chase Cancer Center, Philadelphia, PA (US); Reaction Biology Corporation, Malvern, PA (US)

( * ) Notice: Subject to any disclaimer, the term of this patent is extended or adjusted under 35 U.S.C. 154(b) by 67 days.

(21) Appl. No.: 13/429,755

(22) Filed: Mar. 26, 2012

(65) Prior Publication Data

US 2012/0245173 A1 Sep. 27, 2012

Related U.S. Application Data

(60) Provisional application No. 61/467,013, filed on Mar. 24, 2011.

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC .................. 514/266.1; 544/283; 544/284

(58) Field of Classification Search
USPC .............. 514/266.1, 266.2; 544/283, 284
See application file for complete search history.

(56) References Cited

PUBLICATIONS

Wang, et al., "Structural basis of inhibitor selectivity in MAP kinases", Structure, Sep. 1998; 15;6(9):1117-28.
Deacon, et al., "An isoform-selective, small-molecule inhibitor targets the autoregulatory mechanism of p21-activated kinase", Chem. Biol., Apr. 2008; 15(4):322-31.
Girdler, et al., "Molecular basis of drug resistance in aurora kinases", Chem. Biol., Jun. 2008; 15(6):552-62.
Lipinski, et al., "Experimental and computational approaches to estimate solubility and permeability in drug discovery and development settings", Adv. Drug Deliv. Rev., Mar. 1, 2001; 46(1-3):3-26.
Heron, et al., "SAR and inhibitor complex structure determination of a novel class of potent and specific Aurora kinase inhibitors", Bioorg. Med. Chem. Lett., Mar. 1, 2006; 16(5)1 320-3.
Graczyk, "Gini coefficient: a new way to express selectivity of kinase inhibitors against a family of kinases", J. Med. Chem., Nov. 15, 2007; 50(23):5773-9.
Kiyono, et al., "Stimulation of Ras Guanine Nucleotide Exchange Activity of Ras-GRF1/CDC25Mm upon Tyrosine Phosphorylation by the Cdc420regulated Kinase ACK1", J. Biol. Chem., vol. 275, Sep. 22, 2000, pp. 29788-29793.
Smyth, et al., "Measuring and interpreting the selectivity of protein kinase inhibitors", J. Chem. Biol., (2009) 2:131-151.

*Primary Examiner* — Paul V. Ward
(74) *Attorney, Agent, or Firm* — Stradley Ronon Stevens & Young, LLP

(57) ABSTRACT

Compounds, compositions, and methods for specific inhibition of activated cdc42-associated kinase 1 (Ack1) are provided.

24 Claims, 10 Drawing Sheets

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Completely synthesized

<400> SEQUENCE: 1

Glu Ala Ile Tyr Ala Ala Pro Phe Ala Lys Lys Lys
1               5                   10

INHIBITION OF ACTIVATED CDC42-ASSOCIATED KINASE 1

CROSS REFERENCE TO RELATED APPLICATIONS

This application claims priority to U.S. Provisional Application No. 61/467,013 filed on Mar. 24, 2011, the contents of which are incorporated by reference herein, in their entirety and for all purposes.

REFERENCE TO A SEQUENCE LISTING

This application includes a Sequence Listing submitted electronically as a text file named Ack1 Sequence Listing_ST25.txt, created on Mar. 26, 2012, with a size of 1,000 bytes. The Sequence Listing is incorporated by reference herein.

FIELD OF THE INVENTION

The invention relates generally to the field of formulation chemistry. More particularly, the invention relates to compounds, compositions, and methods for specifically inhibiting activated cdc42-associated kinase 1 (ACK1) and for treating ACK1-associated diseases including, for example, breast, ovarian, pancreatic, lung and prostate cancers and L-dopa induced dyskinesia.

BACKGROUND OF THE INVENTION

Various publications, including patents, published applications, technical articles and scholarly articles are cited throughout the specification. Each of these cited publications is incorporated by reference herein, in its entirety and for all purposes.

Protein kinases are among the important classes of therapeutic targets because of their central roles in cell signaling pathways. The presence of a highly conserved ATP-binding site in kinases consists of a deep hydrophobic pocket, adapted for small molecule binding, that can be exploited by agents. Due to the evolutionary conservation of this pocket between protein kinases, however, achieving highly selective kinase inhibition by ATP-competitive inhibitors is a significant challenge. In drugs, these off-target activities can produce dose-limiting toxicities that limit therapeutic efficacy. In research compounds, off-target activities confound experimental interpretation. Thus, defining the specificity of kinase inhibitors using broad panels of diverse protein kinases is important.

Knowledge of target selectivity for kinase inhibitors is important for predicting and interpreting the effects of inhibitors in both the research and clinical settings. Recent technological advances have led to the development of several methods to profile kinase target selectivity against significant fractions of the 518 human protein kinases. These include kinase-inhibitor binding (or displacement) assays, cell-based profiling methods, and high-throughput enzymatic assays. Initial applications of these methods have revealed a striking degree of promiscuity of these compounds, even those thought highly specific. Off-target inhibition is frequently observed even of kinases only distantly related to the primary target. These findings have emphasized the importance of comprehensive testing of kinase inhibitor specificity.

Generally, kinase inhibitors have been identified in a target-centric manner in which inhibitors are developed through an iterative process against a particular kinase of interest. The resulting compounds are then tested for specificity against a panel of representative kinases. An alternative approach has been suggested in which large libraries of compounds are initially screened in parallel against comprehensive panels of recombinant protein kinases. Compounds showing desired selectivity patterns are then chemically optimized for the desired target(s). The cost of implementing this strategy for very large compound libraries, however, is prohibitive.

SUMMARY OF THE INVENTION

The invention features compounds, for example, a compound of Formula I:

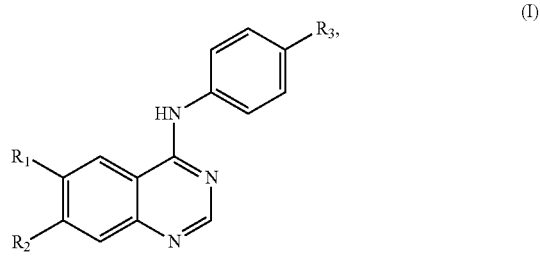

or a pharmaceutically acceptable salt thereof,
wherein each of $R_1$ and $R_2$ is selected from the group consisting of: $R_4$—O—, H, and

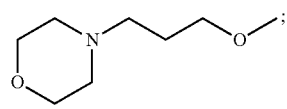

and
$R_3$ is

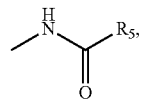

wherein $R_4$ is a $C_1$-$C_6$ alkyl or H;
$R_5$ is a $C_3$-$C_8$ cycloaklyl such as cyclopropyl, benzyl,

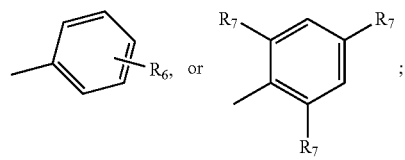

and
$R_6$ is F, Cl, or OMe; and
$R_7$ is a $C_1$-$C_3$ alkylene.

In preferred embodiments, $R_1$ is $H_3CO$—, $R_2$ is a morpholinopropoxy group, and $R_3$ is

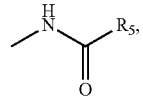

where $R_5$ is a benzyl group or a substituted benzyl group. In some aspects, when $R_1$ is $H_3CO$— and $R_2$ is morpholino, $R_3$ is not cyclopropyl or

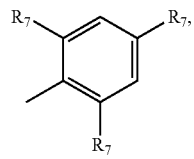

where $R_7$ is methyl, and when $R_1$ and $R_2$ are each hydrogen, $R_3$ is not

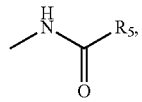

where $R_5$ is benzyl. The compound of Formula I may be comprised in a composition with a carrier such as a pharmaceutically acceptable carrier.

The invention also features methods for inhibiting the biologic activity of activated cdc42-associated kinase I (Ack1). In some aspects, the methods comprise contacting Ack1 with an effective amount of a compound of Formula I, or a composition comprising a compound of Formula I and a carrier. Preferably, the compound is capable of inhibiting the biologic activity of Ack1 at an $IC_{50}$ of about 5 nM or less.

In some aspects, the methods comprise contacting Ack1 with an effective amount of a compound of Formula II:

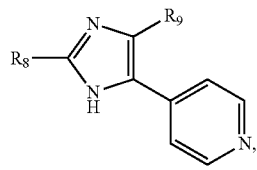

(II)

or a pharmaceutically acceptable salt thereof,
wherein $R_8$ is selected from the group consisting of:

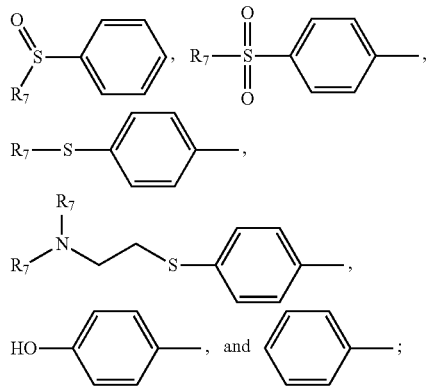

and
$R_9$ is selected from the group consisting of:

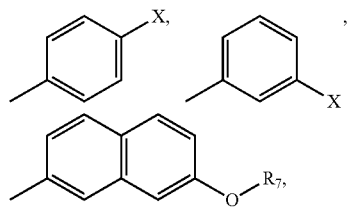

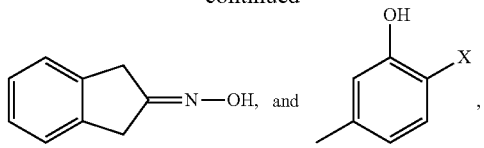

wherein $R_7$ is a $C_1$-$C_3$ alkyl; and X is F, Cl, I, Br, or H. In some aspects, the methods comprise contacting Ack1 with an effective amount of a composition comprising a compound of Formula II and a carrier. Preferably, the compound is capable of inhibiting the biologic activity of Ack1 at an $IC_{50}$ of about 5 nM or less.

In some aspects, the methods comprise contacting Ack1 with an effective amount of a compound of Formula III:

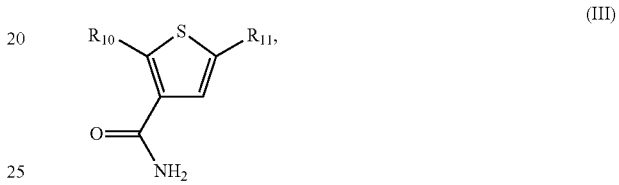

(III)

or a pharmaceutically acceptable salt thereof,
wherein $R_{10}$ is selected from the group consisting of:

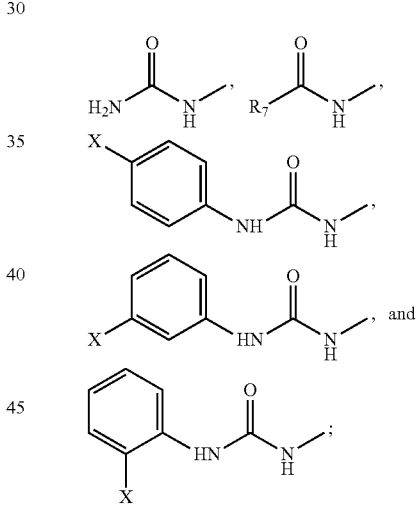

and $R_{11}$ is selected from the group consisting of:

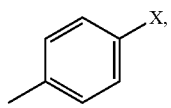

benzyl and propyl, wherein $R_7$ is a $C_1$-$C_3$ alkyl; and X is F, Cl, I, Br, or H. In some aspects, the methods comprise contacting Ack1 with an effective amount of a composition comprising a compound of Formula III and a carrier. Preferably, the compound is capable of inhibiting the biologic activity of Ack1 at an $IC_{50}$ of about 5 nM or less.

The invention also features methods for inhibiting the biologic activity of activated cdc42-associated kinase I (Ack1) in a cell. In some aspects, the methods comprise contacting a cell expressing Ack1 with an effective amount of a compound of Formula I, or a composition comprising a compound of Formula I and a carrier. In some aspects, the methods comprise contacting a cell expressing Ack1 with an effective amount of a compound of Formula II, or a composition comprising a compound of Formula II and a carrier. In some aspects, the methods comprise contacting a cell expressing Ack1 with an effective amount of a compound of Formula III, or a composition comprising a compound of Formula III and a carrier. Preferably, the compound is capable of inhibiting the biologic activity of Ack1 at an $IC_{50}$ of about 5 nM or less. The cell may be a cancer cell such as a prostate cancer cell, a breast cancer cell, a lung cancer cell, a pancreatic cancer cell, an esophageal cancer cell, or a squamous cell carcinoma cancer cell, or may be a neuron.

BRIEF DESCRIPTION OF THE DRAWINGS

FIG. 5A shows results of a Western blot for phospho-Ack1; HEK293 cells expressing Ack1 were treated for 15 min with Formula I, and cell lysate was analyzed. FIG. 5B shows the kinase specificity of Formula I against the panel of 300 protein kinases as in FIG. 2A.

DETAILED DESCRIPTION OF THE INVENTION

Figure 1A:
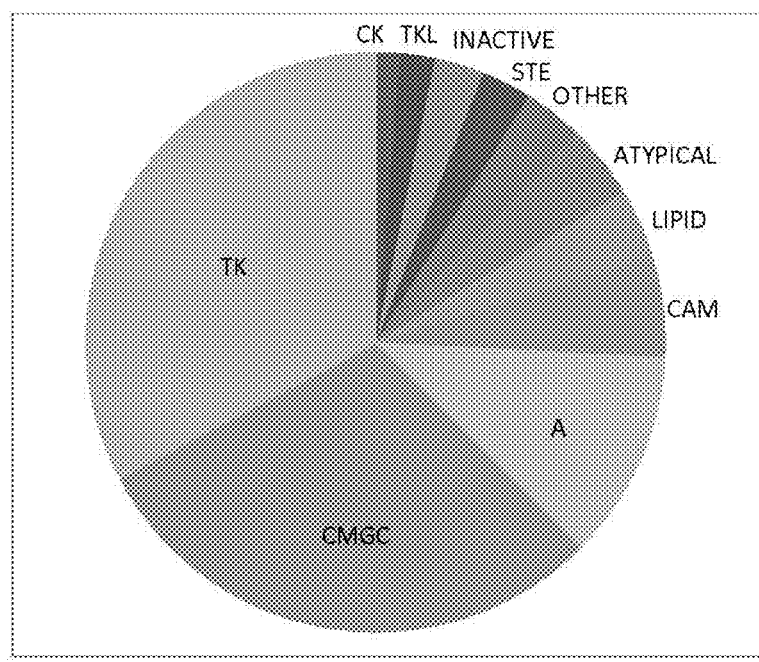
FIG. 1A shows a pie chart showing the representation of different kinase families for the intended targets for the kinase inhibitors in the screening library.

Various terms relating to aspects of the invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

Subject and patient are used interchangeably. A subject may be any animal, including mammals such as companion animals, laboratory animals, and non-human primates. Human beings are preferred.

Inhibiting comprises reducing, decreasing, blocking, preventing, delaying, inactivating, desensitizing, stopping, and/or downregulating the biologic activity or expression of a molecule or pathway of interest.

It has been observed in accordance with the invention that certain compounds can inhibit the biologic activity of activated cdc42-associated kinase 1 (Ack1) without substantially inhibiting the biologic activity of other kinases, or at least can inhibit the biologic activity of Ack1 to a greater extent than other kinases, and with about a 5 nM $IC_{50}$. Selective inhibition of Ack1 has implications for treatment of certain types of cancers as well as L-dopa induced dyskinesia (LID) and other diseases, disorders, or conditions that are caused by, facilitated by, exacerbated by, or otherwise involve biochemical pathways modulated or regulated by the biologic activity Ack1. Accordingly, the invention features compounds, compositions, and methods for inhibiting the biologic activity of Ack1.

The invention features methods for inhibiting the biologic activity of activated cdc42-associated kinase I (Ack1). The methods may be carried out in vitro, in vivo, or in situ.

In some aspects, the methods comprise contacting Ack1 with an effective amount of a compound having Formula I:

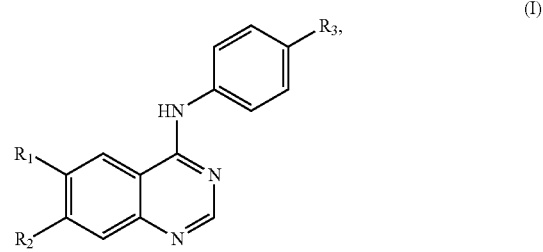

(I)

or a pharmaceutically acceptable salt thereof, wherein each of $R_1$ and $R_2$ is selected from the group consisting of: $R_4$—O—, H, and

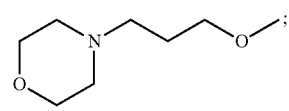

and $R_3$ is

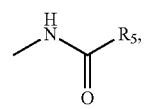

wherein $R_4$ is a $C_1$-$C_6$ alkyl or H;

$R_5$ is a $C_3$-$C_8$ cycloalkyl such as cyclopropyl, benzyl,

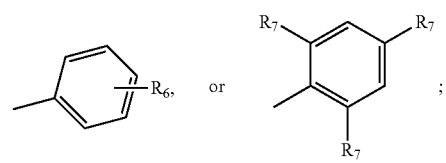

and $R_6$ is F, Cl, or OMe; and $R_7$ is a $C_1$-$C_3$ alkyl.

In preferred embodiments, $R_1$ is $H_3CO—$, $R_2$ is a morpholinopropoxy group, and $R_3$ is

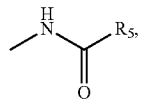

where $R_5$ is a benzyl group or a substituted benzyl group.

In some aspects, the methods comprise contacting Ack1 with an effective amount of a compound having Formula II:

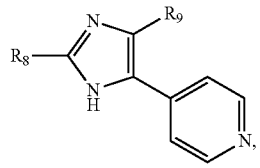

(II)

or a pharmaceutically acceptable salt thereof,
wherein $R_8$ is selected from the group consisting of:

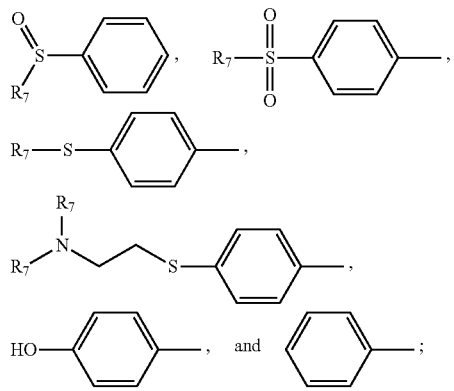

and
$R_9$ is selected from the group consisting of:

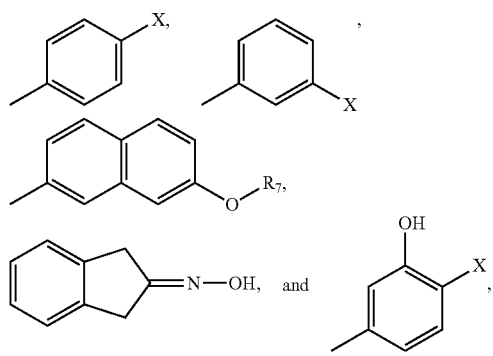

wherein $R_7$ is a $C_1$-$C_3$ alkyl; and X is F, Cl, I, Br, or H.

In preferred embodiments, $R_8$ is a sulfur-containing group, $R_9$ is a halogen-substituted benzyl group wherein the halogen is a fluoro group.

In other aspects, the methods comprise contacting Ack1 with an effective amount of a compound having Formula III:

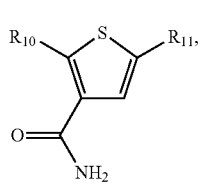

(III)

or a pharmaceutically acceptable salt thereof,
wherein $R_{10}$ is selected from the group consisting of:

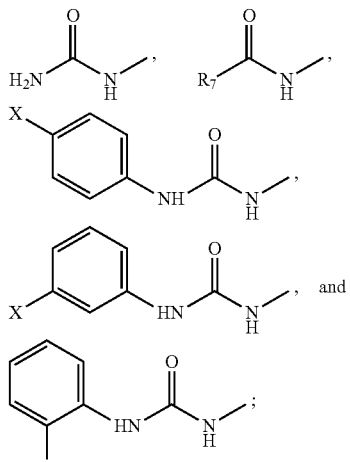

and $R_{11}$ is selected from the group consisting of:

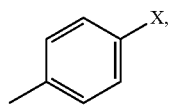

benzyl and propyl, wherein $R_7$ is a $C_1$-$C_3$ alkyl; and X is F, Cl, I, Br, or H.

Preferably, the biologic activity of Ack1 is inhibited by the compound with less than about a 100 nM $IC_{50}$, more preferably inhibited by the compound (Formula I, II, and/or III) with less than about a 50 nM $IC_{50}$, more preferably inhibited by the compound with less than about a 40 nM $IC_{50}$, more preferably inhibited by the compound with less than about a 30 nM $IC_{50}$, more preferably inhibited by the compound with less than about a 20 nM $IC_{50}$, more preferably inhibited by the compound with less than about a 10 nM $IC_{50}$, more preferably inhibited by the compound with less than about a 8 nM $IC_{50}$, and more preferably inhibited by the compound with less than about a 5 nM $IC_{50}$.

In some aspects, the methods comprise contacting Ack1 with an effective amount of a composition comprising a compound having Formula I, Formula II, and/or Formula III and a carrier, which may be a pharmaceutically acceptable carrier. The composition may comprise any dosage form and/or any excipients, including those described or exemplified herein. Preferably, the biologic activity of Ack1 is inhibited by the composition with less than about a 100 nM $IC_{50}$, more preferably inhibited by the composition with less than about a 50 nM $IC_{50}$, more preferably inhibited by the composition with less than about a 40 nM $IC_{50}$, more preferably inhibited by the composition with less than about a 30 nM $IC_{50}$, more preferably inhibited by the composition with less than about a 20 nM $IC_{50}$, more preferably inhibited by the composition with less than about a 10 nM $IC_{50}$, more preferably inhibited by the composition with less than about a 8 nM $IC_{50}$, and more preferably inhibited by the composition with less than about a 5 nM $IC_{50}$.

The invention also features methods for inhibiting the biologic activity of activated cdc42-associated kinase I (Ack1) in a cell or in a tissue. The methods may be carried out in vitro, in vivo, or in situ.

In some aspects, the methods comprise contacting a cell expressing Ack1 with an effective amount of a compound having Formula I:

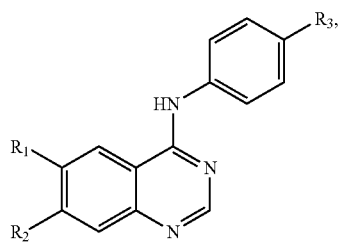
(I)

or a pharmaceutically acceptable salt thereof,
wherein each of $R_1$ and $R_2$ is selected from the group consisting of: $R_4$—O—, H, and

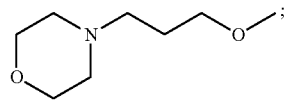

and
$R_3$ is

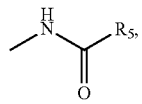

wherein $R_4$ is a $C_1$-$C_6$ alkyl or H;
$R_5$ is a $C_3$-$C_8$ cycloalkyl such as cyclopropyl, benzyl,

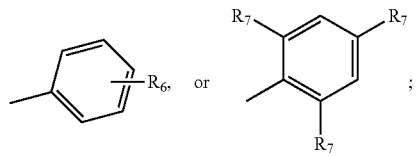

and
$R_6$ is F, Cl, or OMe; and
$R_7$ is a $C_1$-$C_3$ alkyl.

In some aspects, the methods comprise contacting a cell expressing Ack1 with an effective amount of a compound having Formula II:

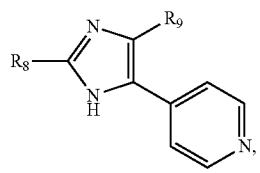
(II)

or a pharmaceutically acceptable salt thereof,
wherein $R_3$ is selected from the group consisting of:

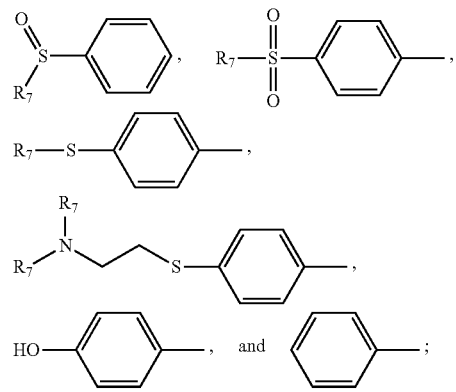

and
$R_9$ is selected from the group consisting of:

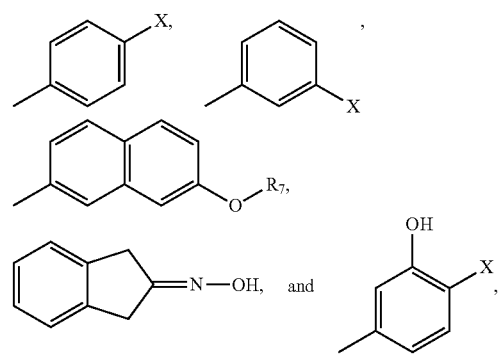

wherein $R_7$ is a $C_1$-$C_3$ alkyl; and X is F, Cl, I, Br, or H.

In some aspects, the methods comprise contacting a cell expressing Ack1 with an effective amount of a compound having Formula III:

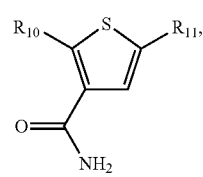
(III)

or a pharmaceutically acceptable salt thereof,
wherein $R_{10}$ is selected from the group consisting of:

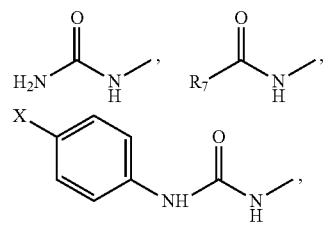

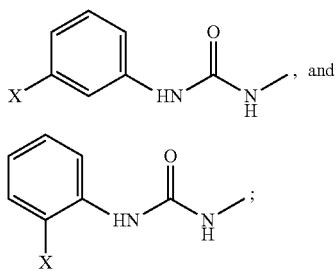

and $R_{11}$ is selected from the group consisting of:

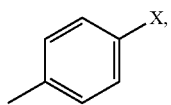

benzyl and propyl, wherein $R_7$ is a $C_1$-$C_3$ alkyl; and X is F, Cl, I, Br, or H.

Preferably, the biologic activity of Ack1 is inhibited by the compound with an $IC_{50}$ of about 100 nM or less, more preferably inhibited by the compound with an $IC_{50}$ of about 50 nM or less, more preferably inhibited by the compound an $IC_{50}$ of about 40 nM or less, more preferably inhibited by the compound with an $IC_{50}$ of about 30 nM or less, more preferably inhibited by the compound with an $IC_{50}$ of about 20 nM or less, more preferably inhibited by the compound with an $IC_{50}$ of about 10 nM or less, more preferably inhibited by the compound with an $IC_{50}$ of about 8 nM or less, and more preferably inhibited by the compound with an $IC_{50}$ of about 5 nM or less.

In some aspects, the methods comprise contacting a cell expressing Ack1 with an effective amount of a composition comprising a compound having Formula I, Formula II, and/or Formula III and a carrier, which may be a pharmaceutically acceptable carrier. The composition may comprise any dosage form and/or any excipients, including those described or exemplified herein. Preferably, the biologic activity of Ack1 is inhibited by the composition with less than about a 100 nM $IC_{50}$, more preferably inhibited by the composition with less than about a 50 nM $IC_{50}$, more preferably inhibited by the composition with less than about a 40 nM $IC_{50}$, more preferably inhibited by the composition with less than about a 30 nM $IC_{50}$, more preferably inhibited by the composition with less than about a 20 nM $IC_{50}$, more preferably inhibited by the composition with less than about a 10 nM $IC_{50}$, more preferably inhibited by the composition with less than about a 8 nM $IC_{50}$, and more preferably inhibited by the composition with less than about a 5 nM $IC_{50}$.

In any of the methods, the cell may be any cell in which Ack1 is expressed. The cell may be a cell stably transformed with a nucleic acid encoding Ack1. The cell may be a cell line. The cell may be a cancer cell such as a prostate cancer cell, a breast cancer cell, a lung cancer cell, a pancreatic cancer cell, an esophageal cancer cell, or a squamous cell carcinoma cancer cell, or may be a neuron. Some examples of cells include LNCaP, LAPC-4, HMEC, 4T1, 293T, and Cos 7 cells.

In some aspects, the invention features compounds. One compound is a compound of Formula I:

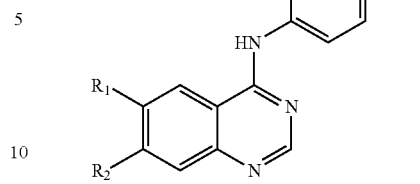

or a pharmaceutically acceptable salt thereof,
wherein each of $R_1$ and $R_2$ is selected from the group consisting of: $R_4$—O—, H, and

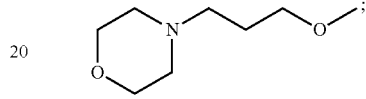

and
$R_3$ is

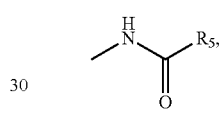

wherein $R_4$ is a $C_1$-$C_6$ alkyl or H;
$R_5$ is a $C_3$-$C_8$ cycloalkyl, benzyl,

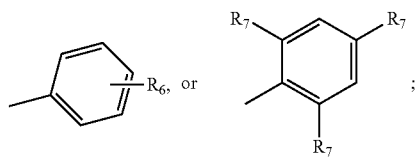

and
$R_6$ is F, Cl, or OMe; and
$R_7$ is a $C_1$-$C_3$ alkyl, provided that when $R_1$ is $H_3CO$— and $R_2$ is morpholino, $R_3$ is not cyclopropyl or

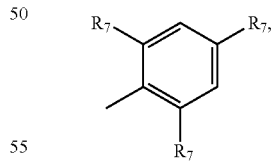

where $R_7$ is methyl, and provided that when $R_1$ and $R_2$ are each hydrogen, $R_3$ is not

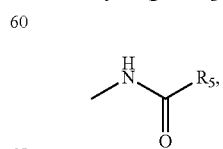

where $R_5$ is benzyl.

In preferred embodiments, $R_1$ is $H_3CO-$, $R_2$ is a morpholinopropoxy group, and $R_3$ is

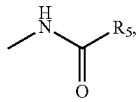

where $R_5$ is a benzyl group or a substituted benzyl group.

One compound is a compound of Formula II:

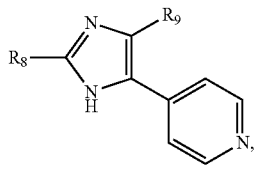

(II)

or a pharmaceutically acceptable salt thereof,
wherein $R_8$ is selected from the group consisting of:

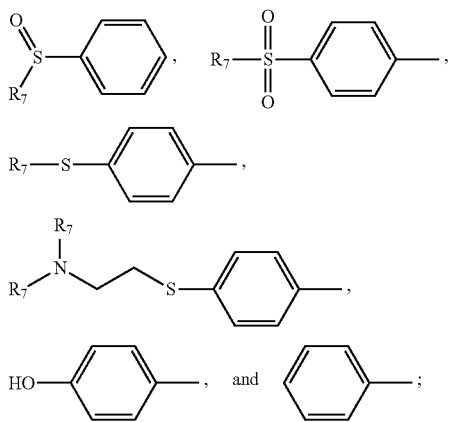

and
$R_9$ is selected from the group consisting of:

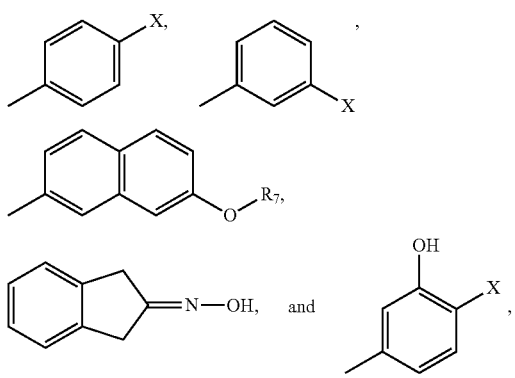

wherein $R_7$ is a $C_1$-$C_3$ alkyl; and X is F, Cl, I, Br, or H.

One compound is a compound of Formula III:

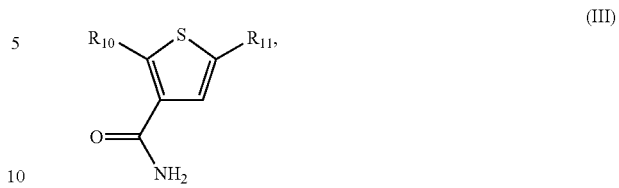

(III)

or a pharmaceutically acceptable salt thereof,
wherein $R_{10}$ is selected from the group consisting of:

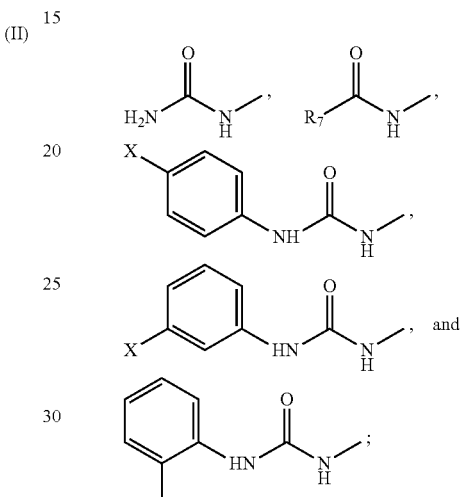

and $R_{11}$ is selected from the group consisting of:

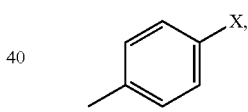

benzyl and propyl, wherein $R_7$ is a $C_1$-$C_3$ alkyl; and X is F, Cl, I, Br, or H.

Pharmaceutically acceptable salts may be acid or base salts. Non-limiting examples of pharmaceutically acceptable salts include sulfates, methosulfates, methanesulfates, pyrosulfates, bisulfates, sulfites, bisulfites, nitrates, besylates, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, dioates, benzoates, chlorobenzoates, methylbenzoates, dinitromenzoates, hydroxybenzoates, methoxybenzoates, phthalates, sulfonates, toluenesulfonates, xylenesulfonates, pheylacetates, phenylpropionates, phenylbutyrates, citrates, lactates, γ-hydroxybutyrates, glycollates, tartrates, methanesulfonates, propanesulfonates, mandelates, and other salts customarily used or otherwise FDA-approved.

The compounds may be formulated as a composition, for example, with a carrier. Compositions may comprise a compound of Formula I, Formula II, or Formula III, or a pharmaceutically acceptable salt thereof. The carrier is preferably a pharmaceutically acceptable carrier. Pharmaceutically acceptable carriers include aqueous vehicles such as water, alcohol (e.g., ethanol or glycol), saline solutions, dextrose solutions, and balanced salt solutions, as well as nonaqueous vehicles such as alcohols and oils, including plant or vegetable-derived oils such as olive oil, cottonseed oil, corn oil, canola oil, sesame oil, and other non-toxic oils. The compositions may comprise one or more pharmaceutically acceptable excipients.

The compositions preferably comprise an effective amount of the compound such as a compound having Formula I, Formula II, Formula III, or pharmaceutically acceptable salt of any of Formula I, II, or III. The compositions may be prepared to provide from about 0.05 mg to about 500 mg of the compound, or pharmaceutically acceptable salt thereof. The compositions may comprise from about 1 mg to about 200 mg of the compound, may comprise from about 10 mg to about 200 mg of the compound, may comprise from about 10 mg to about 100 mg of the compound, may comprise from about 50 mg to about 100 mg of the compound, may comprise from about 20 mg to about 400 mg of the compound, may comprise from about 100 mg to about 300 mg of the compound, and may comprise from about 50 mg to about 250 mg of the compound, or pharmaceutically acceptable salt thereof.

The compositions may be formulated for administration to a subject in any suitable dosage form. The compositions may be formulated for oral, buccal, nasal, transdermal, parenteral, injectable, intravenous, subcutaneous, intramuscular, rectal, or vaginal administrations. The compositions may be formulated in a suitable controlled-release vehicle, with an adjuvant, or as a depot formulation.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions.

Solid dosage forms include tablets, pills, powders, bulk powders, capsules, granules, and combinations thereof. Solid dosage forms may be prepared as compressed, chewable lozenges and tablets which may be enteric-coated, sugar coated or film-coated. Solid dosage forms may be hard or encased in soft gelatin, and granules and powders may be provided in non-effervescent or effervescent form. Solid dosage forms may be prepared for dissolution or suspension in a liquid or semi-liquid vehicle prior to administration.

Liquid dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions may be oil-in water or water-in-oil emulsions.

Pharmaceutically acceptable excipients utilized in solid dosage forms include coatings, binders, lubricants, diluents, disintegrating agents, coloring agents, flavoring agents, preservatives, sweeteners, and wetting agents. Enteric-coated tablets, due to their enteric-coating, resist the action of stomach acid and dissolve or disintegrate in the neutral or alkaline intestines. Other examples of coatings include sugar coatings and polymer coatings. Sweetening agents are especially useful in the formation of chewable tablets and lozenges. Pharmaceutically acceptable excipients used in liquid dosage forms includes solvents, suspending agents, dispersing agents, emulsifying agents, surfactants, emollients, coloring agents, flavoring agents, preservatives, and sweeteners.

Non-limiting examples of binders include glucose solution, acacia mucilage, gelatin solution, sucrose and starch paste. Non-limiting examples of lubricants include talc, starch, magnesium or calcium stearate, lycopodium and stearic acid. Non-limiting examples of diluents include lactose, sucrose, starch, kaolin, salt, mannitol and dicalcium phosphate. Non-limiting examples of disintegrating agents include corn starch, potato starch, bentonite, methylcellulose, agar and carboxymethylcellulose. Non-limiting examples of emulsifying agents include gelatin, acacia, tragacanth, bentonite, and surfactants such as polyoxyethylene sorbitan monooleate. Non-limiting examples of suspending agents include sodium carboxymethylcellulose, pectin, tragacanth, veegum and acacia.

Non-limiting examples of coloring agents include any of the approved certified water soluble FD and C dyes, mixtures thereof, and water insoluble FD and D dyes suspended on alumina hydrate. Non-limiting examples of sweetening agents include dextrose, sucrose, fructose, lactose, mannitol and artificial sweetening agents such as saccharin, aspartame, sucralose, acelsulfame potassium, and other artificial sweeteners. Non-limiting examples of flavoring agents include synthetic flavors and natural flavors extracted from plants such as fruits and mints, and synthetic blends of compounds which produce a pleasant sensation. Non-limiting examples of wetting agents include propylene glycol monostearate, sorbitan monooleate, diethylene glycol monolaurate and polyoxyethylene laural ether. Non-limiting examples of enteric-coatings include fatty acids, fats, waxes, shellac, ammoniated shellac and cellulose acetate phthalates. Non-limiting examples of film coatings include hydroxyethylcellulose, sodium carboxymethylcellulose, polyethylene glycol 4000 and cellulose acetate phthalate. Non-limiting examples of preservatives include glycerin, methyl and propylparaben, ethylparaben, butylparaben, isobutylparaben, isopropylparaben, benzylparaben, citrate, benzoic acid, sodium benzoate and alcohol.

Elixirs include clear, sweetened, hydroalcoholic preparations. Pharmaceutically acceptable carriers used in elixirs include solvents. Syrups include concentrated aqueous solutions of a sugar, for example, sucrose, and may contain a preservative. An emulsion is a two-phase system in which one liquid is dispersed throughout another liquid. Pharmaceutically acceptable carriers used in emulsions may include emulsifying agents and preservatives. Suspensions may use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, include organic acids and a source of carbon dioxide. Sources of carbon dioxide include sodium bicarbonate and sodium carbonate. Coloring and flavoring agents may be used in all such dosage forms.

Additional excipients that may be included in any dosage forms include, but are not limited to antimicrobial agents, isotonic agents, buffers, antioxidants, local anesthetic agents, sequestering or chelating agents, analgesic agents, antiemetic agents, and other agents to enhance selected characteristics of the formulation.

Antimicrobial agents may be cidal or static, and may be antimicrobial, antifungal, antiparasitic, or antiviral. Non-limiting examples of commonly used antimicrobial agents include phenols or cresols, mercurials, benzyl alcohol, chlorobutanol, methyl and propyl p-hydroxybenzoic acid esters, thimerosal, benzalkonium chloride and benzethonium chloride. Acidic or basic pH may be used for antimicrobial effects in some aspects. Non-limiting examples of isotonic agents include sodium chloride and dextrose. Non-limiting examples of buffers include phosphate and citrate buffers. A non-limiting example of a chelating agent for metal ions is EDTA.

The invention also features methods for treating L-dopa induced dyskinesia in a subject in need thereof. In some aspects, the methods comprise administering to the subject an effective amount of a composition comprising a compound having Formula I, Formula II, and/or Formula III and a pharmaceutically acceptable carrier. The composition may comprise any dosage form and/or any excipients, including those described or exemplified herein.

The following examples are provided to describe the invention in greater detail. They are intended to illustrate, not to limit, the invention.

Example 1

Experimental Methods 40 ng of recombinant Ack1 was incubated with saturating quantities of peptide substrate (Glu-Ala-Ile-Tyr-Ala-Ala-Pro-Phe-Ala-Lys-Lys-Lys) (SEQ ID NO:1) and in the presence of a compound in Ack1 kinase buffer (20 mM Tris pH 7.4, 10 mM $MgCl_2$, 0.1 mM $NaVO_4$, 0.5 mM dithiothreitol). [$^{32}$P]-γ-ATP was added in a total concentration of 10 μM ATP to initiate the reaction. Following 30 minute incubation at 30° C., phosphorylated peptide substrate was captured by spotting the reaction on P81 cationic filter paper and unincorporated [$^{32}$P]-γ-ATP was removed by washing in a solution of phosphoric acid. Phosphorylated peptide was then quantified by autoradiography or by PhosphorImager analysis or by scintillation counting.

Example 2

Experimental Results

To directly test the kinase selectivity of a large number of established kinase inhibitors, high throughput kinase assays were employed against a panel of ~300 recombinant human protein kinases. An economical method based on conventional filter-binding assays was used at a nanoliter scale using radiolabeled ATP that directly measures kinase catalytic activity toward a polypeptide and/or protein substrate. In contrast to previous large-scale kinase profiling studies, which typically focused on clinically relevant kinase inhibitors, compounds that are primarily used as tools for research were screened. The library of inhibitors comprises 160 pure compounds known to inhibit kinases representing all major protein kinase families, as well as a limited number of compounds that were not developed to target protein kinases (FIG. 1A).

Figure 1B:
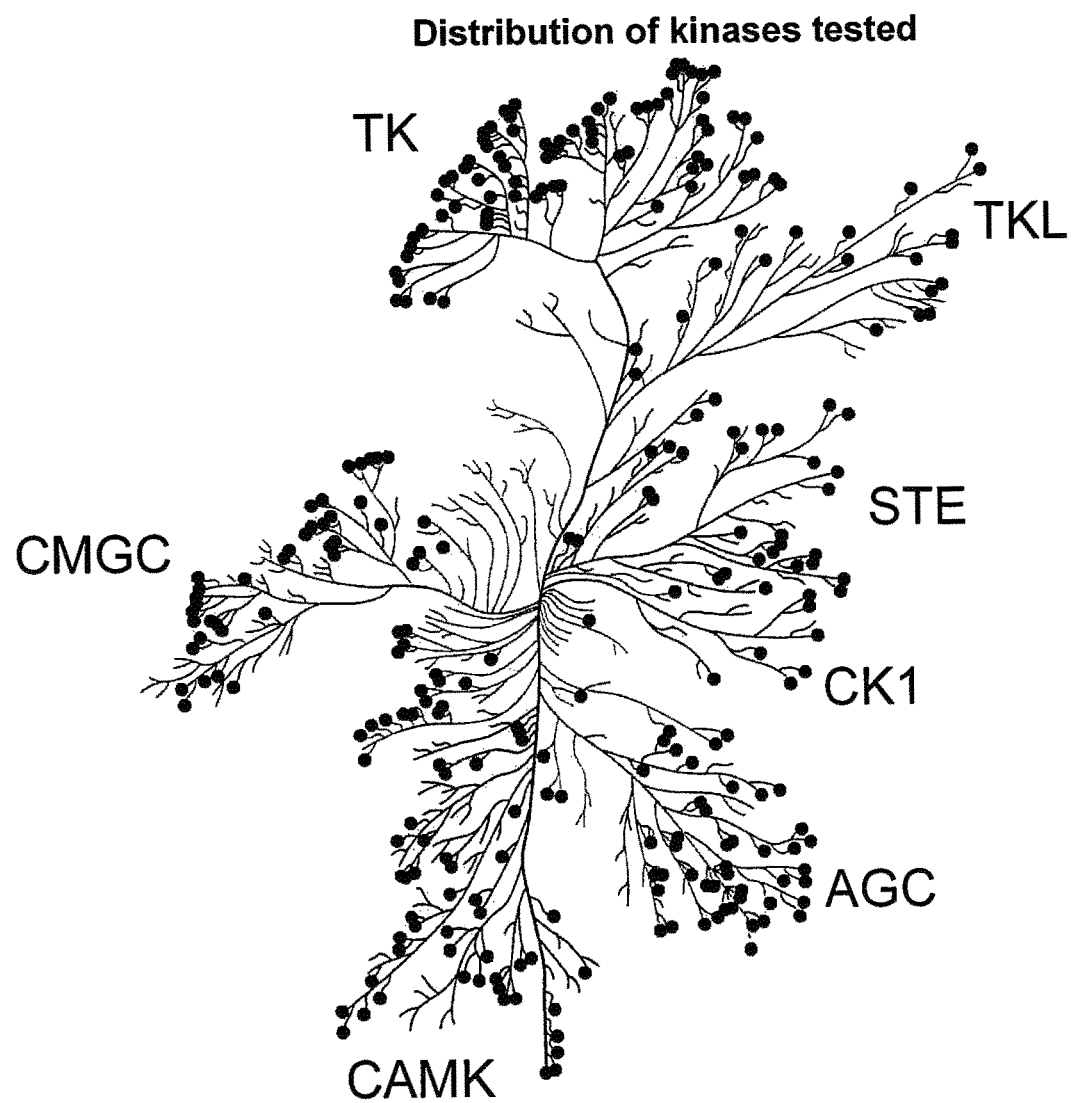
FIG. 1B shows the distribution of kinases tested in the kinase panel. Dots representing individual protein kinases in the panel are shown on a dendrogram representing the complete human kinome (based on amino acid sequence similarity between kinases within the catalytic domain).

The kinase panel tested represents all major human protein kinase. The distribution of kinases is shown in FIG. 1B. For simplicity, all compounds were tested at a concentration of 0.5 μM in the presence of 10 μM ATP. The 0.5 μM concentration was chosen despite an average reported $IC_{50}$ for these compounds toward their primary targets of 66 nM in order to capture weaker off-target inhibitory activity.

Figure 1C:
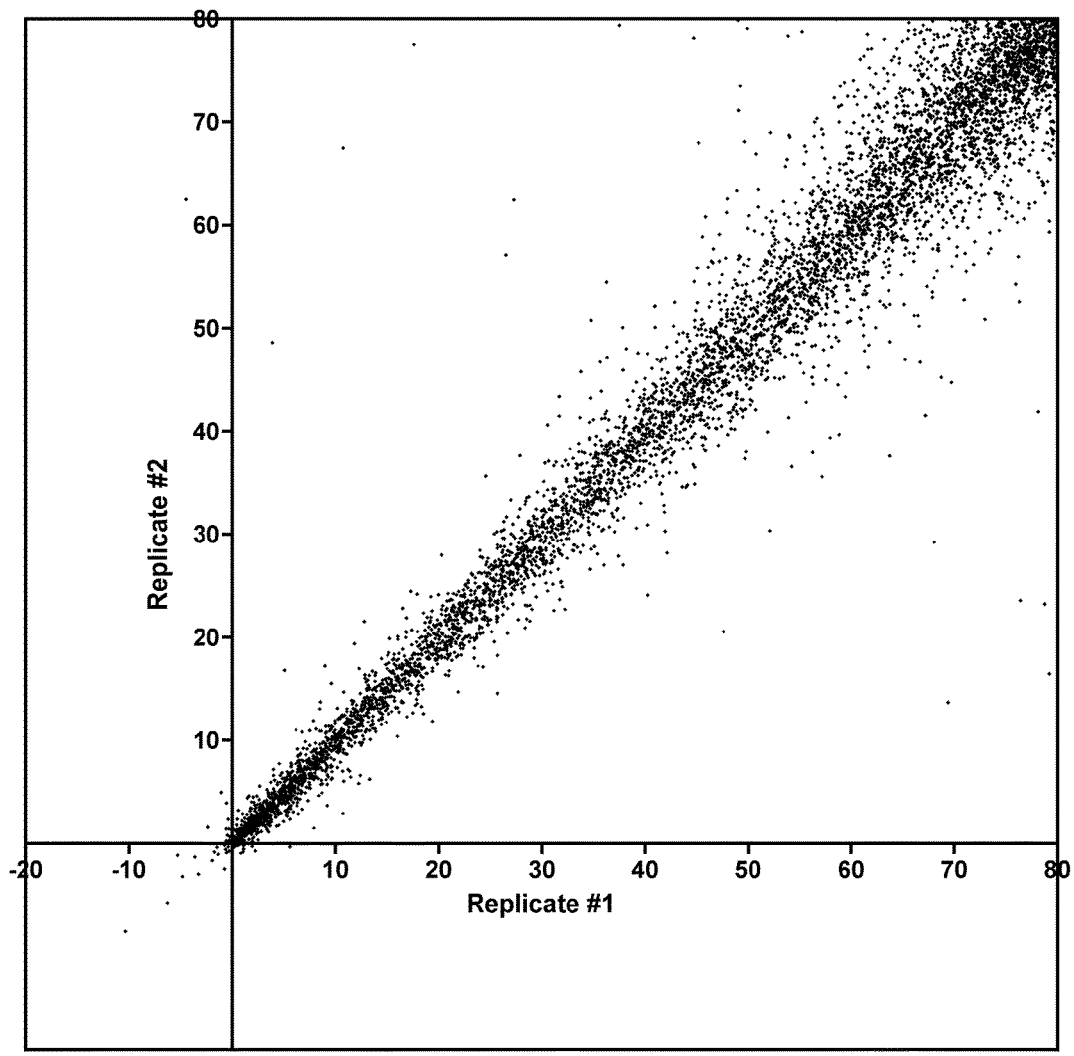
FIG. 1C shows a scatter plot representing the reproducibility of the screening data. Each point represents one kinase-inhibitor pair plotted as the residual kinase activity in one replicate versus activity in the second replicate, for all kinase-inhibitor pairs in which at least 20% inhibition was observed.

Each kinase-inhibitor pair was tested in duplicate and results were expressed as percent remaining kinase activity compared to solvent (DMSO) control reactions. Disparate replicates were eliminated from the analysis. FIG. 1C illustrates the reproducibility of the resulting dataset as an x-y plot in which each point represents one kinase-inhibitor pair plotted as the residual kinase activity in one replicate versus activity in the second replicate, for all kinase-inhibitor pairs in which at least 20% inhibition was observed.

Example 3

New Small Molecule Inhibitors of Ack1

As described above, a large-scale parallel screening of a collection of 160 known kinase inhibitors was conducted against a panel of 294-300 recombinant human protein kinases. Goals included the identification of novel inhibitor scaffolds for new kinase targets and the revelation of the target specificities of this panel of research compounds. Each inhibitor was tested in duplicate at 500 nM against each kinase using radiolabeled ATP (10 μM total ATP) and a peptide or protein substrate. The resulting dataset comprises almost 100,000 independent functional assays measuring pairwise inhibition of each kinase by each compound. The data revealed many new targets for these compounds and simultaneously revealed the selectivity of these compounds among protein kinases.

Figure 2A:
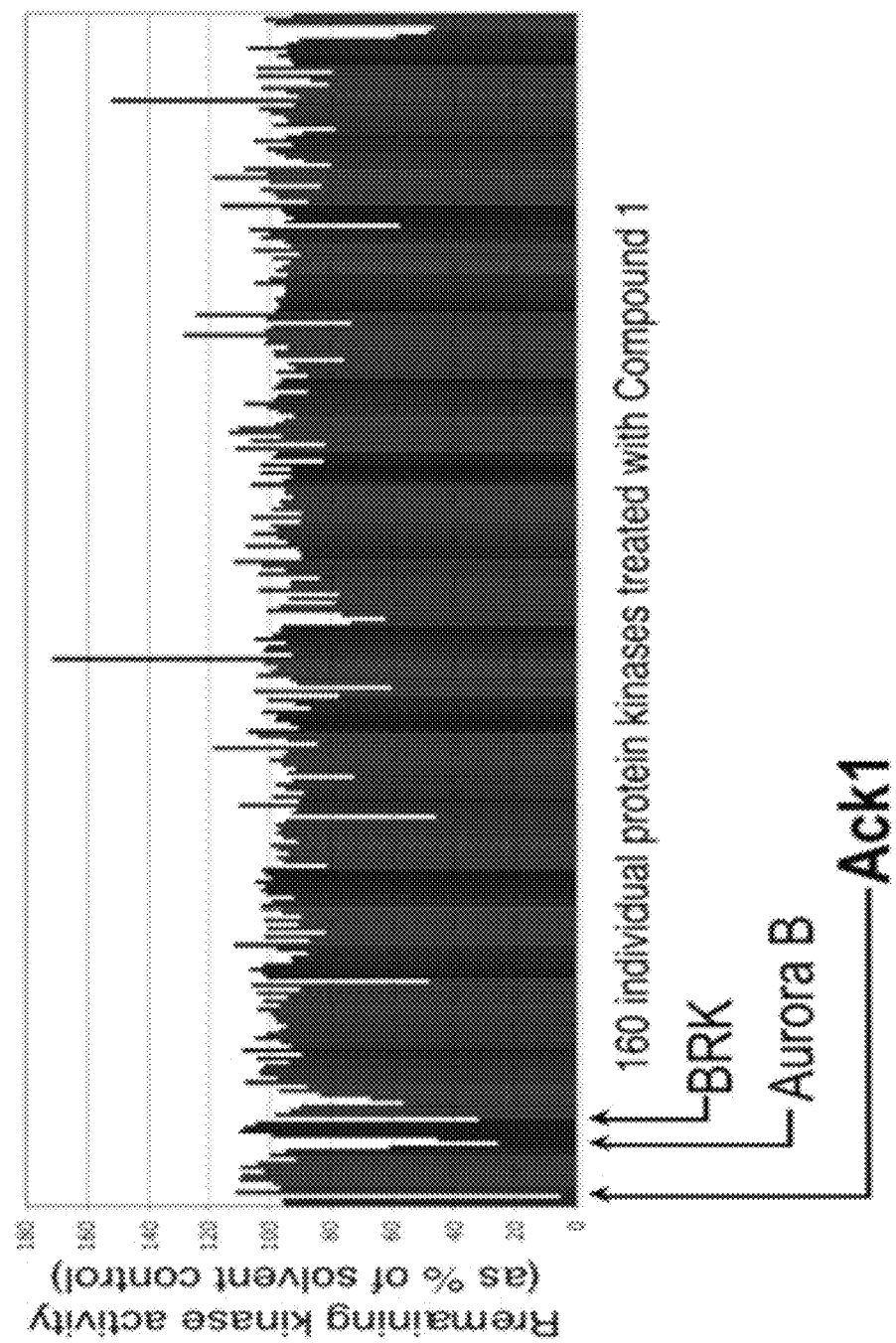
FIG. 2A shows the catalytic activity of 300 kinases in the presence of 500 nM 1; average of duplicates are shown.

The data were analyzed for compounds that inhibit Ack1. Some compounds, like staurosporine, inhibited Ack1 in addition to many other kinases. Therefore, Ack1 inhibitory compounds that showed significant target selectivity were sought. Inhibitor selectivity was quantitatively assessed using the Gini coefficient (Piotr P et al. (2007) J. Med. Chem., 50:5773-9; and, Lynette A et al. (2009) J. Chem. Biol. 2:131-51). One compound inhibiting Ack1, compound 1, was unusually selective and showed significantly greater inhibitory activity against Ack1 than against any other kinase. Interestingly, compound 1 was developed as an ATP-competitive inhibitor of the serine/threonine kinase Aurora (Heron N M et al. (2006) Bioorg. Med. Chem. Lett. 16:1320-3) and, indeed, the kinase most potently inhibited after Ack1 (95% inhibition) is Aurora B (75% inhibition). The only other kinase inhibited (by >50%) by 500 nM 1 is the non-receptor tyrosine kinase BRK (FIG. 2A).

Compound 1 is an anilinoquinazoline, a highly validated class of compounds that target protein kinases. Physicochemical properties of compound 1 are consistent with Lipinski rules for drug-likeness (Lipinski C A et al. (2001) Adv. Drug Deliv. Rev. 46:3-26): (<5 hydrogen bond donors (actual value=2), <10 hydrogen bond donors (7), molecule weight<500 Da (400.43 Da), log P<5 (2.876), and a polar surface area<140 Angstrom2 (85.4 A2). Note that at 400 Da, compound 1 lies at the threshold of compounds believed capable of passively crossing the blood-brain barrier. Thus, compound 1 is a drug-like molecule that achieves unusual selectivity for Ack1 over other kinases for an ATP-competitive kinase inhibitor.

Example 4

Preliminary Structure-Activity (SAR) Analysis

Figure 2B:
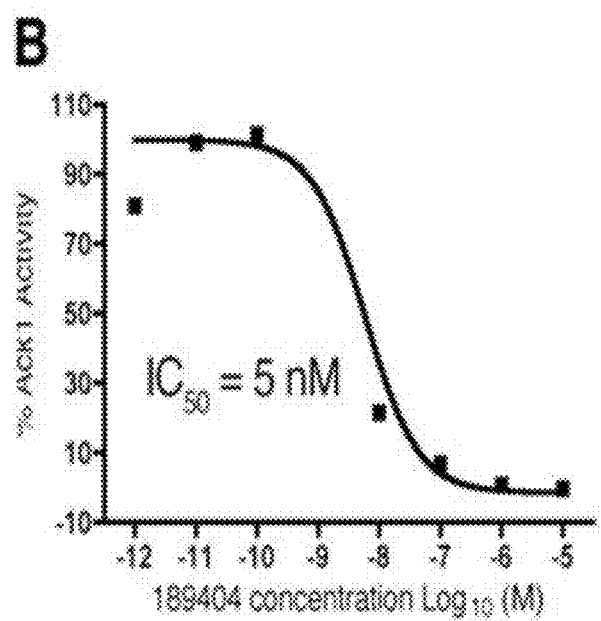
FIG. 2B shows a dose-response of Formula I compound against Ack1.

Ten compounds containing anilinoquinazoline cores or closely related structures were present in the screening library, and many showed significant inhibition of Ack1, consistent with a central role of this core in contributing to Ack activity. Substitutions of the aniline ring showed drastic effects on inhibitory activity, suggesting that the structure of this region is important for activity (data not shown). Dose-response studies of compound 1 revealed an $IC_{50}$ of 5 nM against Ack1 in vitro (FIG. 2B). By contrast, treatment of HEK293 cells with up to micromolar concentrations of compound 1 did not reduce Ack1 autophosphorylation on the activation loop site Tyr284 (data not shown), suggesting poor cell permeability of compound 1. Thus, this Example proposed derivatives of compound 1 that inhibit Ack1 in the cellular context while retaining its target specificity.

Figure 3:
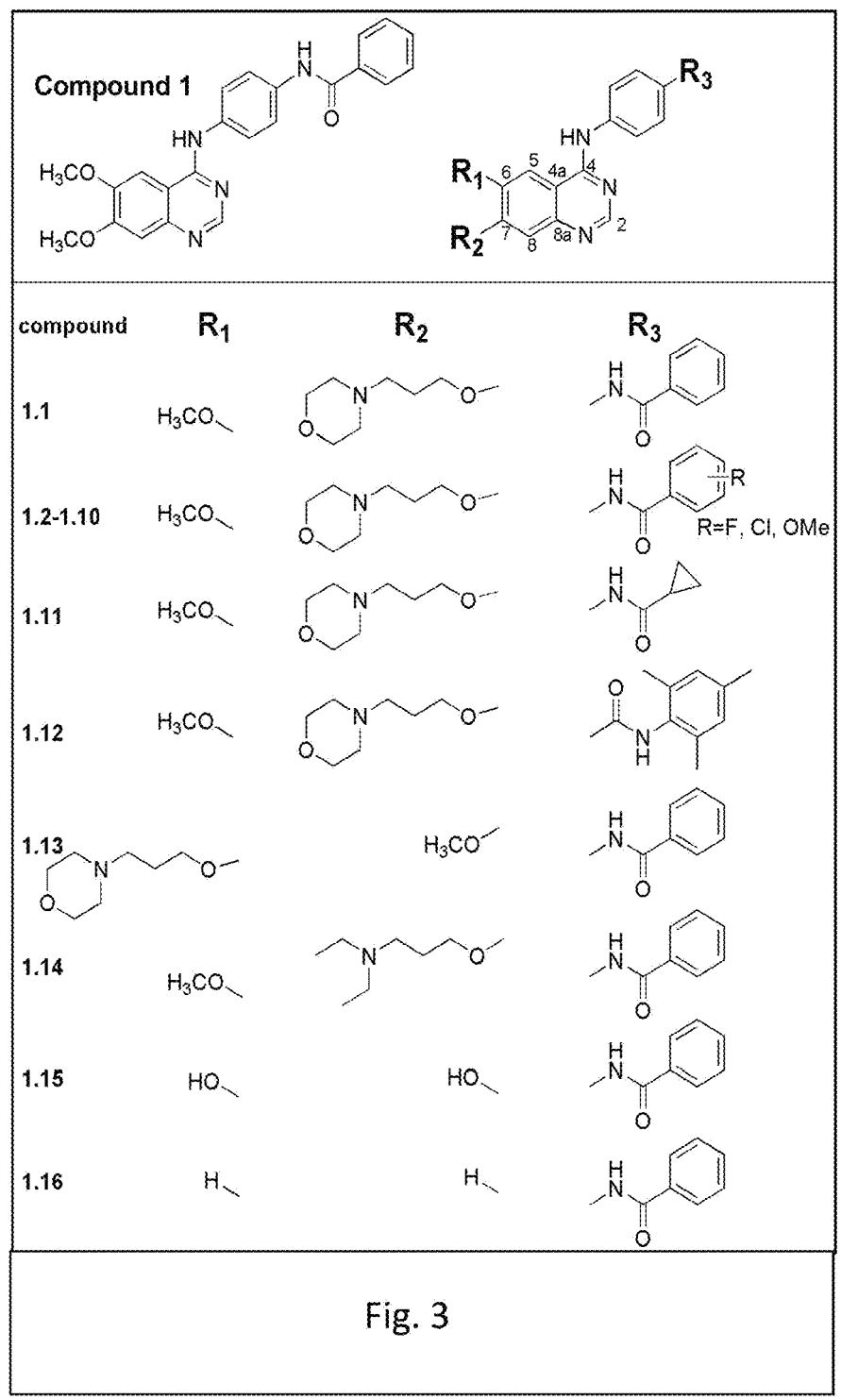
FIG. 3 shows the structure of compound 1 (Formula I) and sample analogs. Compound 1 has an $IC_{50}$ of 5 nM in vitro. Compound 1.1 has similar potency and inhibits Ack1 in cells (FIG. 5).
Figure 4:
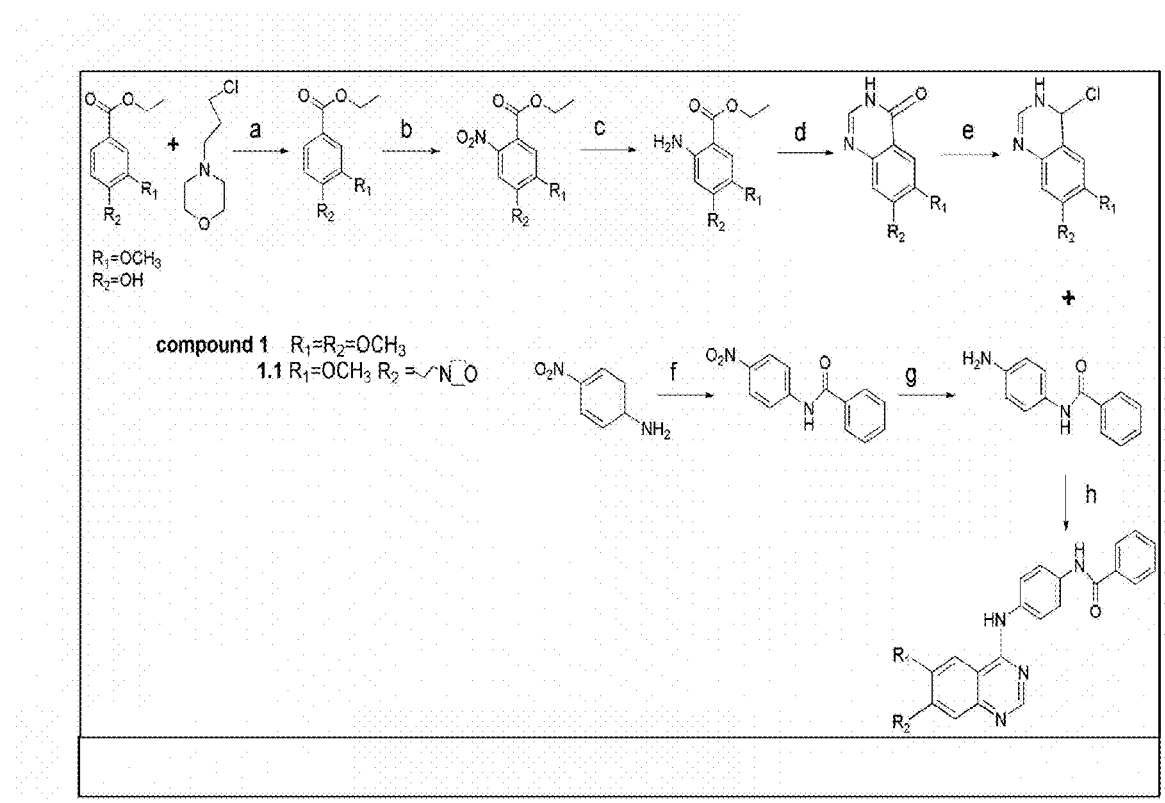
FIG. 4 shows the synthesis of compounds 1 and 1.1 by an in house organic synthesis facility.

Compound 1 was initially identified as a screening hit for inhibitors of Aurora kinase. It was found that compound 1 showed poor cellular efficacy against Aurora despite good in vitro activity (Heron N M et al. (2006) Bioorg. Med. Chem. Lett. 16:1320-3). Two modifications of compound 1 improved cellular activity against Aurora: replacement of the central phenyl ring with a pyrimidine and replacement of the methoxy group at the 7 position in the quinazoline with a 3-(1-morpholino)propoxy group (compound 1.1, FIG. 3). To test if these modifications would also improve cellular efficacy against Ack1, they were synthesized (see FIG. 4 for synthetic scheme) in house.

Figure 5:
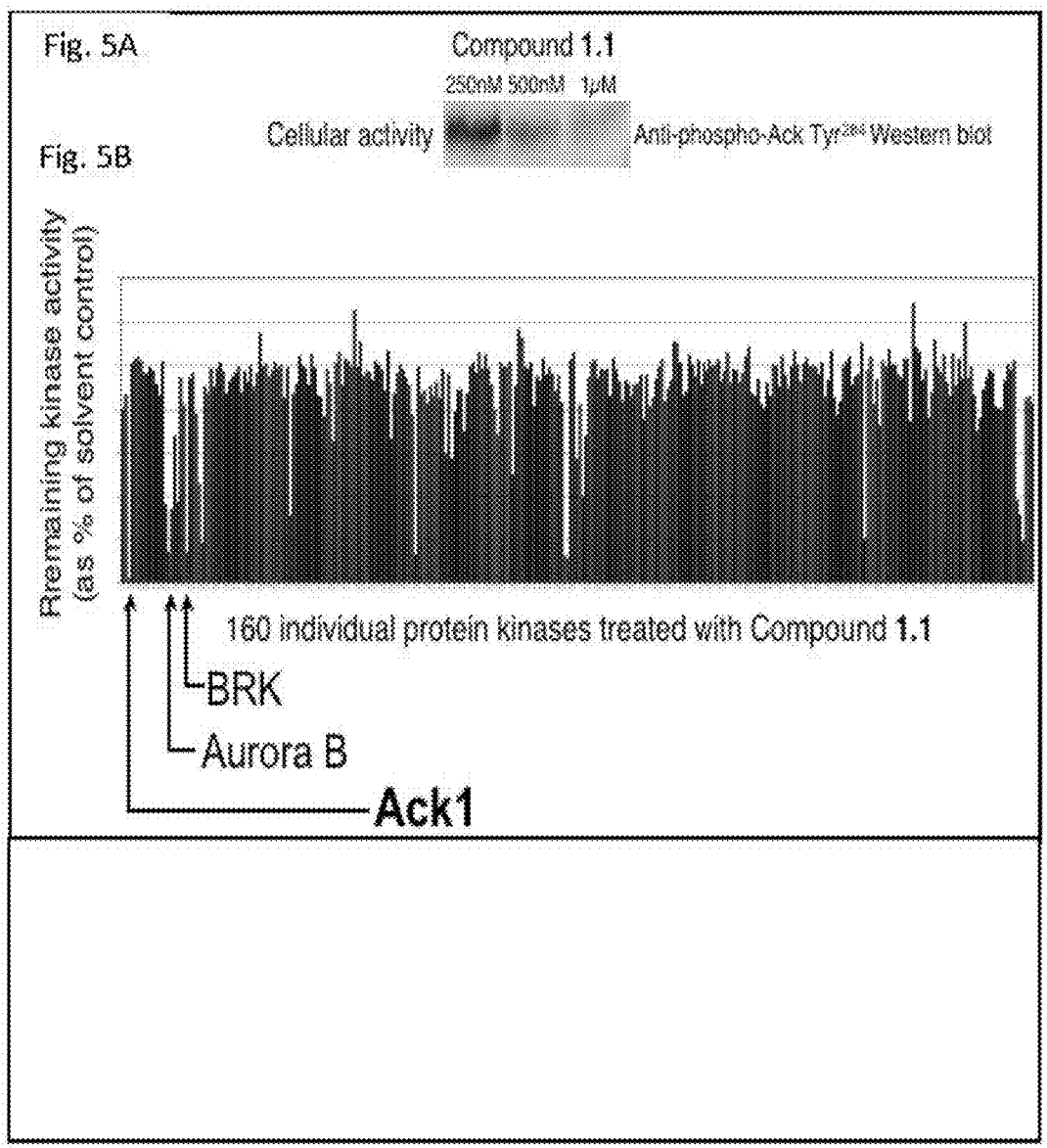
FIG. 5 shows that the Formula I compound inhibits Ack1 autophosphorylation in cells and has high target specificity.

The benzene to pyrimidine substitution reduced Ack1 inhibitory activity>100-fold and showed no cell activity (data not shown). By contrast, compound 1.1 showed comparable in vitro activity to compound 1 (data not shown), but now potently inhibited Ack1 autophosphorylation in cells (FIG. 5A). Kinase profiling showed that compound 1.1 inhibited Ack1 more potently than any other kinases and the spectrum of off-target kinase targets was similar to compound 1, though overall the selectivity of compound 1.1 (by Gini score) was slightly reduced compared to compound 1 (compare FIGS. 2A and 4B). Thus, substitutions of the quinazoline provide an opportunity to improve cell permeability without compromising inhibitory activity or selectivity.

Compound 1.1 (also known as ZM447439) and a derivative have been co-crystallized with Aurora kinases, revealing the molecular details of the interaction (Heron N M et al. (2006) Bioorg. Med. Chem. Lett. 16:1320-3; and, Girdler F et al. (2008) Chem. Biol. 15:552-62). Although the orientation and conformation of the compound in each structure are highly similar, the compound bound Aurora B as a Type I inhibitor, but Aurora A in the Type II mode. In both structures, the orientation of the compound places the terminal benzamide deep within the ATP-binding pocket, while the morpholino-propoxy substituent of the quinazoline ring at the other end of the molecule extends out of the pocket, consistent with the role of this moiety in promoting cell permeability rather than contributing significantly to kinase binding.

Substitutions of the benzamide have dramatic effects on the activity of this scaffold against Aurora (Heron N M et al. (2006) Bioorg. Med. Chem. Lett. 16:1320-3). For example, chloride substitution at C3 of the phenyl ring enhances potency 30-fold while 4-ethylphenyl reduces activity by ~30 fold. Thus, substituents of the benzamide and quinazoline rings modulate Aurora inhibitory activity in vitro and in cells. Because the Ack1 construct used in the primary screen comprises only the kinase domain of Ack1 and a limited additional region C-terminal (amino acids 110-476), it is likely that this compound class also targets the Ack1 ATP-binding pocket. It is believed that compound 1.1 binds Ack1 in an analogous manner to its binding to Aurora, and it is believed that substitution of the benzamide and quinazoline rings can be used to enhance relative activity of this compound series against Ack compared to Aurora and other targets.

The crystal structure of Ack1 has been solved in both an unliganded form and with compounds bound in the ATP-binding pocket. Superposition of the structure of Ack1 bound to AMPPNP (PDB 1U54) with the structure of Aurora B bound to compound 1.1 (PDB 2VRX) reveals no obvious steric clashes of 1.1 with residues of Ack1 (data not shown). Twenty five residues of Aurora are within six angstroms of 1.1 in the co-structure. Sixty percent of these residues are identical between Aurora and Ack1, consistent with a similar binding mode for the compound to Ack1. Nevertheless, sequence differences between the kinases suggest the possibility that alterations in the compound could differentially affect kinase binding.

Example 5

Additional Structural Classes of Ack1 Inhibitors

Figure 6:
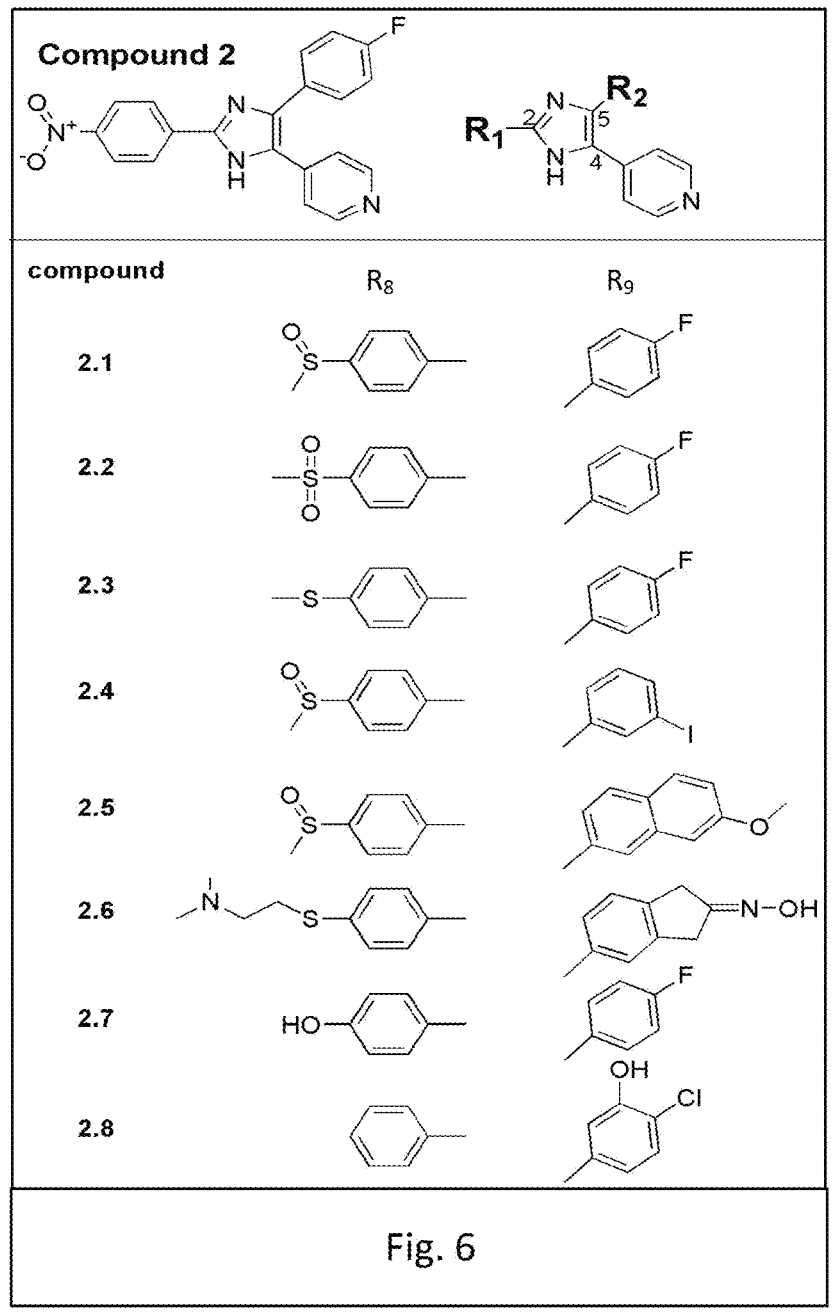
FIG. 6 shows the structure of compound 2 (Formula II) and analogs.
Figure 7:
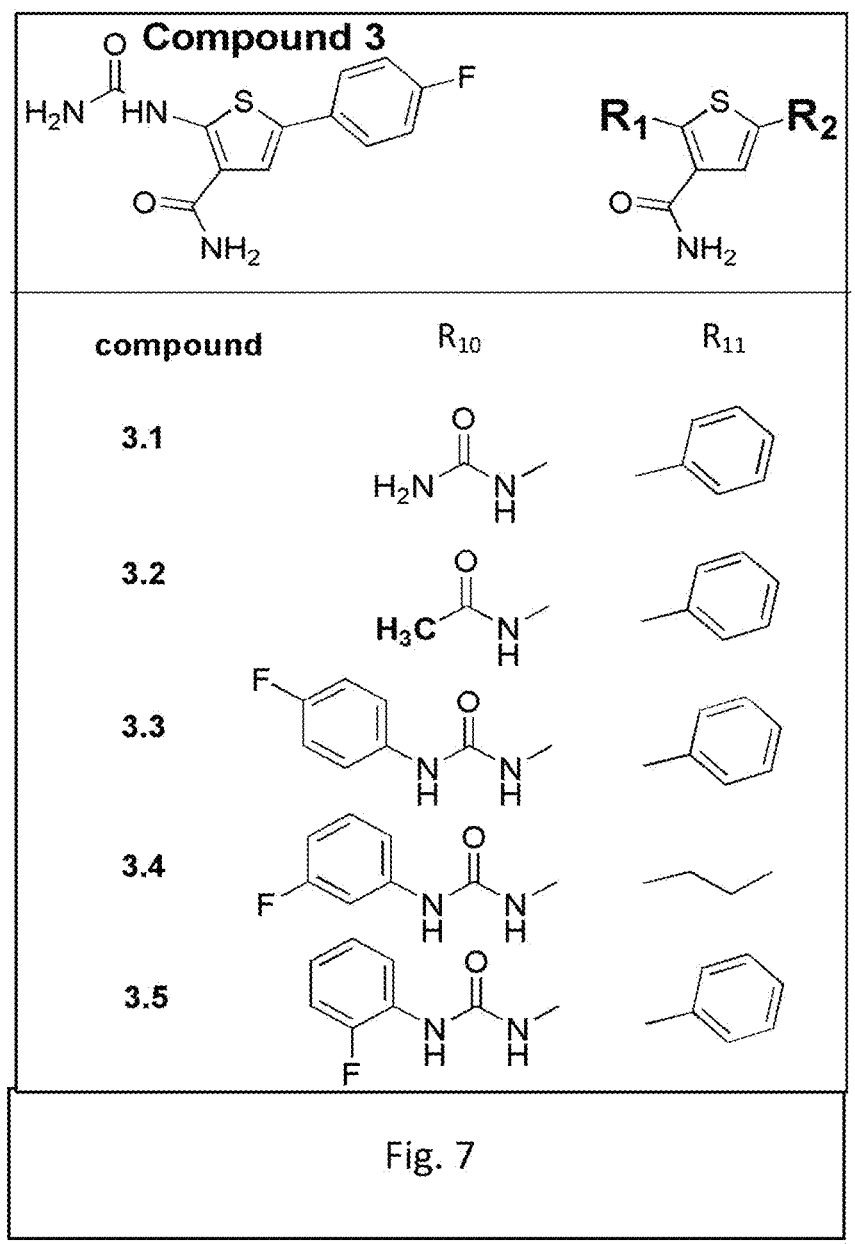
FIG. 7 shows the structure of compound 3 (Formula III) and analogs.

To evaluate other Ack1 inhibitors identified by potential leads, each compound was analyzed with regard to its potency in the primary screen and specificity (Gini score). Several of the most potent and specific Ack1 inhibitors were anilino-quinazolines related to compound 1. Among the remaining promising compounds, compounds 2 and 3 (FIGS. 6 and 7) were selected for further analysis based on their potency against Ack1 relative to other kinases and the commercial availability of structural analogs.

Compound 2 (also known as PD169316) is a 2,4,5-substituted imidazole developed as a cell-permeable, ATP-competitive inhibitor of p38 MAP kinase. In the screen, compound 2 showed potent inhibition of p38 MAPK (98%), consistent with its reported $IC_{50}$. In addition, compound 2 showed reasonable activity against Ack1 (54% inhibition) with additional activity against a limited number of kinases including casein kinase I and NKK. The attractive selectivity of this compound, its significant activity against Ack1, and the availability of structural analogs, lead to focus on this compound as a starting point for the development of a second Ack1 inhibitor.

Compound 3 (also known as TPCA-1) is a substituted thiophene developed as a cell-permeable, ATP-competitive inhibitor of IκB kinase 2 (IKK-2). Indeed, 91% inhibition of IKK-2 was observed, and importantly, 94% inhibition of Ack1 catalytic activity was observed. Additional off-target activities included partial inhibition of the catalytic activities of FLT3, JAK1/2, RET, and Tyk2.

Example 6

Optimization of Compound 1.1

The goals of the experiments described in this example include the characterization of the mechanism of action of compound 1.1, a lead Ack1 inhibitor and the optimization of its potency, selectivity, and cell-permeability, for example, a low nanomolar potency in vitro, activity in cells at <200 nM, and >10 fold selectivity over the next most potently inhibited kinase in kinase profiling experiments.

A. Mechanism of Action of Compound 1.1.

Rationale and approach. Without intending to be limited to any particular theory or mechanism of action, it is hypothesized that compound 1.1 binds Ack1 in a similar manner to the manner in which it binds to Aurora. To test this hypothesis, whether inhibition by 1.1 is ATP-competitive will be assessed. In addition, the molecular details of the compound interaction will be investigated using collaborative modeling and crystallographic approaches.

Experimental details. 40 ng of recombinant Ack1 (Carna Biosciences) will be incubated with saturating quantities of peptide substrate (Glu-Ala-Ile-Tyr-Ala-Ala-Pro-Phe-Ala-Lys-Lys-Lys) (SEQ ID NO:1) and a wide range of concentrations of 1.1 in Ack1 kinase buffer (20 mM Tris pH 7.4, 10 mM $MgCl_2$, 0.1 mM $NaVO_4$, 0.5 mM dithiothreitol). Reactions will be performed and analyzed as done previously (FIG. 2B; (Decon S W et al. (2008) Chem. Biol. 15:322-31)). It is expected that the data will demonstrate competitive binding with ATP. In parallel, models will be generated in house to energetically minimize compound 1.1 and analogs docked into the Ack1 ATP-binding pocket via homology modeling based on the Aurora B-1.1 co-crystal structure (PDB 2VRX). Crystallography will be used to determine the precise binding mode of compound 1.1 or analogs to Ack1 and to guide the analysis of the compound analogs discussed below.

B. Compound 1.1 SAR: Benzamide Substitutions.

Rationale and approach. The benzamide of compound 1.1 binds deep into the ATP-binding pocket of Aurora, and substitutions in this ring alter inhibitor potency. It is believed that that substitutions on the phenyl ring could be used to reduce compound 1.1 activity against Aurora (and other off-target kinases) relative to inhibition of Ack1. To test this hypothesis, an analog library will be synthesized, beginning with a systematic analysis of halides and methoxy groups at para, meta, and ortho positions of the phenyl ring. Additional derivatives, described below, will also be purchased and tested in vitro and for their ability to inhibit Ack1 autophosphorylation in cells. Most potent compounds with cellular activity will be tested for modulation of Erk activation in Ras-GRF1-expressing cells to validate this therapeutic approach for L-dopa induced dyskinesia.

Compounds. Compounds 1.2-1.10 (FIG. 3) will be synthesized in house as has already done for compound 1.1 (FIG. 4), replacing benzoyl chloride in step f with the corresponding substituted benzoyl chloride. The results with these compounds (and structural data obtained above) will be used to guide further SAR exploration. A large variety of substituted benzoyl chlorides are available that include additional groups (e.g., methyl and cyano) added singly and in combination at each ring position that will then be tested in an iterative manner (synthesis→biological assay and structural modeling→synthesis of new analogs). Compound 1.1 analogs replacing the benzamide phenyl ring with cyclopropyl and trimethylbenzyl groups (compounds 1.11 and 1.12) are also commercially available and will be obtained and tested.

Biological assays. For dose-response experiments, Ack1 phosphorylation of peptide substrate will be measured in the presence of solvent control or increasing concentrations of compound as in FIG. 2B. Compounds with $IC_{50}$<500 nM will be assessed for kinase selectivity by screening compounds at 500 nM (10 μM ATP) against their panel of 300 human protein kinases. Selectivity will be quantified using the Gini score as described above.

Compounds which show more potent inhibition of Ack1 than any other kinase will be tested for inhibition of Ack1 autophosphorylation in cells as in FIG. 5A. Compounds that inhibit Ack1 autophosphorylation in cells will next be tested as to whether they inhibit Ras-GRF1 mediated Erk activation in HEK293 cells transiently expressing Ras-GRF1. Cells will be transfected with Ras-GRF1 and either Ack1 alone, or Ack1 with constitutively active Cdc42 (Cdc42V12 mutant) to promote Ack1 activity, as previously described (Kiono M J et al. (2000) J. Biol. Chem. 275:29788-93). Endogenous Erk activation will be monitored by Western blotting lysates using phospho-specific antibodies for active Erk. It is believed that Ack1 inhibitors will inhibit Erk activation in a Ras-GRF1-dependent manner, validating inhibition of LID-relevant pathway by targeting Ack1.

C. Compound 1.1 SAR: Quinazoline Substitutions.

Rationale and approach. The methoxy and morpholino substituents at the quinazoline C6 and C7 positions of compound 1.1, respectively, critically modulate Aurora inhibitory activity and cell permeability. Without intending to be limited to any particular theory or mechanism of action, it is hypothesized that substitutions of the quinazoline may differentially affect the activity of this molecule toward Ack1 and its off-target kinases to improve selectivity. Compound 1.1 analogs will be assessed using the three assays described above.

Compounds and assays. Compounds 1.13-1.15 will be synthesized in house by substituting R1 and R2 in the synthesis scheme of FIG. 4. Compound 1.16, in which the C6 and C7 quinazoline substituents are hydrogen, is commercially available. Additional alkyl halides will be explored at these positions based on the initial studies. Compound activity, selectivity, and cell activity will be tested as above. One goal is to enhance compound selectivity for Ack1 without compromising the important role this region plays in cell permeability of the compound.

Alternative approaches and future directions. It is believed that the experiments to reveal one or more substitutions that increase Ack1 inhibitory activity relative to off-target kinases. One goal is >10-fold selectivity. Compounds will be prioritized according to the following rank order: cellular inhibition of Ack1>in vitro specificity>in vitro potency. This will ensure that resulting compounds remain useful for cellular studies while optimizing specificity and potency. If individual compound modifications of the benzamide and quinazoline regions improve compound performance, they will then be combined pairwise through new syntheses according to the scheme in FIG. 4. If none of the derivatives significantly improve compound 1.1 selectivity or potency, compound optimization will be considered from more one of the more divergent anilionoquinazoline analogs with Ack1 inhibitory activity.

Example 7

Optimization of Compounds 2 and 3

These experiments will test the transition of two additional Ack1 compounds into leads with improved potency, specificity, and cell activity. Commercially available compounds related to two other Ack1 inhibitors previoiusly identified will be analyzed to determine if analogs can be found with enhanced potency and selectivity toward Ack1 and to reveal key features of the SAR.

A. Compound 2 Analogs.

Rationale and approach. The 2,4,5-substituted imidazole, compound 2 (FIG. 6), was identified as an inhibitor of Ack1 (54% inhibition) and has reasonable selectivity for an initial hit. This compound was developed as a cell-permeable, ATP-competitive inhibitor of p38 MAPK and the structure of a closely related compound (SB203580) bound to p38 has been reported (Wang Z et al. (1998) Structure 6:1117-28). The pyridine nitrogen makes key contacts with the kinase hinge region and the fluorophenyl group binds within a hydrophobic pocket. The nitrophenyl group (a 4-(methylsulfinyl)phenyl group in the published structure makes contacts with the phosphate binding region. Because of the near three-fold symmetry of this compound family, the orientation of this compound in the binding pocket of Ack1 is less clear than for compound 1. Therefore, SAR studies of this compound family will exploit diverse commercially available derivatives of 2 in in vitro and cell-based assays.

Experimental details. Whether inhibition of Ack1 by 2 is competitive with ATP will be tested as described in example 6 above. Next, whether the pyridine nitrogen plays an important role in kinase binding as it does for p38 MAPK, will be assessed by testing a compound in which this ring is replaced by phenyl (not shown, commercially available). It is believed that this will significantly reduce activity but, if not, a large number of commercially available compounds with phenyl at this position will be screened to validate this scaffold as a better lead.

If the pyridine is important, compounds in which the substituted phenyls at position 2 and 5 of the imidazole are replaced will be tested. Compounds 2.1-2.3, and 2.7 will test a variety of substituted phenyl groups at imidazole ring carbon 2 in the context of the 4-fluorophenyl substituent at carbon 5. Compounds 2.4-2.6 and 2.8 will elucidate the activity of compounds in which the 4-fluorophenyl group is replaced with other substituted phenyls. All compounds will be tested initially at 500 nM against Ack1 catalytic activity in vitro as above. Most potent derivatives will be subjected to complete dose-response analysis, kinase profiling, and cell-based assays as above.

B. Compound 3 Analogs

Rationale and approach. The substituted thiophene, compound 3, showed 94% inhibition of Ack1 and reasonable selectivity. It was developed as a potent (18 nM), ATP-competitive, and cell-permeable inhibitor of IKK-2. No structural data concerning the binding mode of this compound to IKK-2 has been reported. Five commercially available 3-thiophenecarboxamides related to compound 3 have been identified (FIG. 7), and the importance of the substitutents at the 2 and 5 positions of the thiophene will be systematically tested.

Compounds and assays. Compound 3.1 differs from compound 3 in the loss of the fluorine substituent on R2, compound 3.2 replaces the urea with an acetamide, and compounds 3.3-3.5 extend the urea with either para, meta, or ortho fluorphenyl. Compounds will be assessed and prioritized as above.

Alternative approaches. It is believed that the SAR studies will reveal more potent and/or more selective inhibitors of Ack1 than the initial hit molecules. Nevertheless, if this is not the case, kinase profiling of these diverse compounds (against 300 protein kinases) as proposed may reveal novel inhibitors for kinases other than Ack1 as a byproduct. Unusually potent or specific compounds, or compounds targeting kinases for which no small-molecule inhibitors currently exist, will be offered to experts in their particular targets for further characterization.

The invention is not limited to the embodiments described and exemplified above, but is capable of variation and modification within the scope of the appended claims.

Compound 1.1:

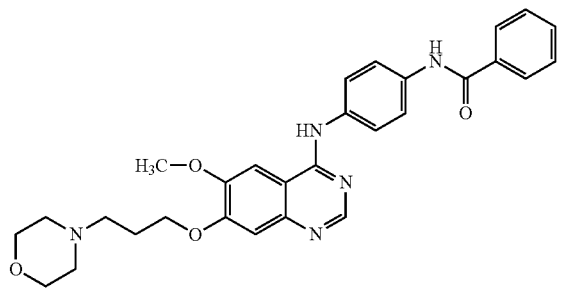

N-[4-[[6-Methoxy-7-[3-(4-morpholinyl)propoxy]-4-quinazolinyl]amino]phenyl]benzamide Compound 2:

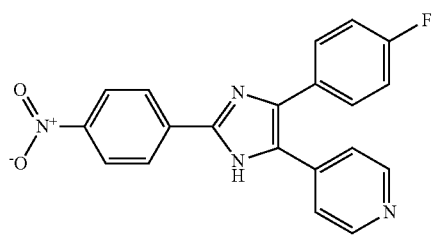

4-[5-(4-fluorophenyl)-2-(4-nitrophenyl)-1H-imidazol-4-yl]-pyridine

Compound 3:

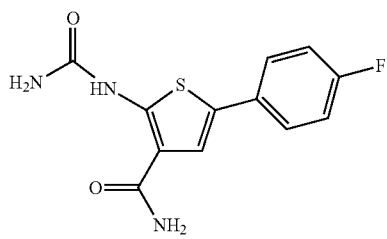

2-[(Aminocarbonyl)amino]-5-(4-fluorophenyl)-3-thiophenecarbonoxamide

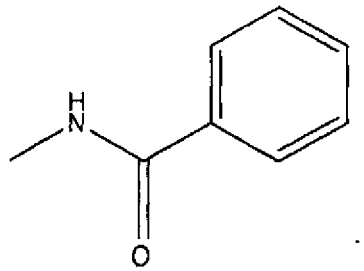

We claim:

1. A method for inhibiting the biologic activity of activated cdc42-associated kinase I (Ack1), comprising contacting Ack1 with an amount of a compound of Formula I effective to inhibit the biologic activity of Ack1:

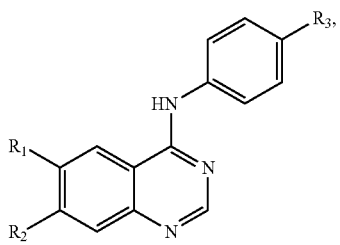
(I)

or a pharmaceutically acceptable salt thereof, wherein each of $R_1$ and $R_2$ is selected from the group consisting of: $R_4$—O—, H, and

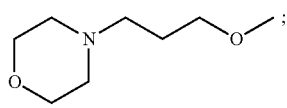

and
$R_3$ is

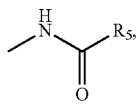

wherein $R_4$ is a $C_1$-$C_6$ alkyl or H;
$R_5$ is a $C_3$-$C_8$ cylcloalkyl, benzyl,

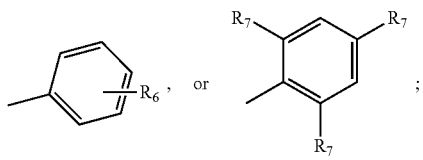

and
$R_6$ is F, Cl, or OMe; and
$R_7$ is a $C_1$-$C_3$ alkyl.

2. The method of claim 1, wherein the method is carried out in vitro.

3. The method of claim 1, wherein the compound is capable of inhibiting the biologic activity of Ack1 at an $IC_{50}$ of about 5 nM or less.

4. A method for inhibiting the biologic activity of activated cdc42-associated kinase I (Ack1) in a cell, comprising contacting a cell expressing Ack1 with an amount of a compound of Formula I effective to inhibit the biologic activity of Ack 1 in the cell:

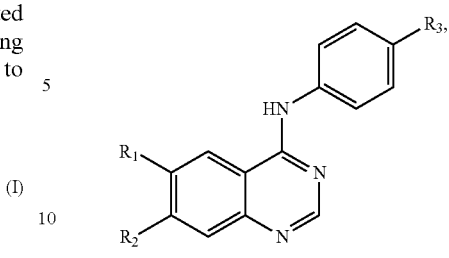
(I)

or a pharmaceutically acceptable salt thereof,
wherein each of $R_1$ and $R_2$ is selected from the group consisting of: $R_4$—O—, H, and

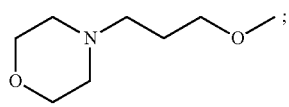

and
$R_3$ is

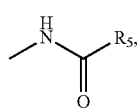

wherein $R_4$ is a $C_1$-$C_6$ alkyl or H;
$R_5$ is a $C_3$-$C_8$ cycloalkyl, benzyl,

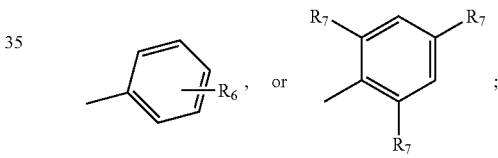

and
$R_6$ is F, Cl, or OMe; and
$R_7$ is a $C_1$-$C_3$ alkyl.

5. The method of claim 4, wherein the method is carried out in vitro.

6. The method of claim 4, wherein the compound is capable of inhibiting the biologic activity of Ack1 at an $IC_{50}$ of about 5 nM or less.

7. The method of claim 4, wherein the cell is a cancer cell.

8. The method of claim 4, wherein the cell is a neuron.

9. The method of claim 1, wherein the compound of Formula I is in a composition comprising a carrier.

10. The method of claim 9, wherein the method is carried out in vitro.

11. The method of claim 9, wherein the compound is capable of inhibiting the biologic activity of Ack1 at an $IC_{50}$ of about 5 nM or less.

12. The method of claim 9, wherein the carrier is a pharmaceutically acceptable carrier.

13. The method of claim 4, wherein the compound of Formula I is in a composition comprising a carrier.

14. The method of claim 13, wherein the method is carried out in vitro.

15. The method of claim 13, wherein the compound is capable of inhibiting the biologic activity of Ack1 at an $IC_{50}$ of about 5 nM or less.

16. The method of claim 13, wherein the cell is a cancer cell.

17. The method of claim 13, wherein the cell is a neuron.

18. The method of claim 13, wherein the carrier is a pharmaceutically acceptable carrier.

19. The method of claim 1 wherein $R_1$ is $H_3CO-$; $R_2$ is

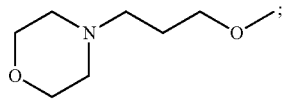

and $R_3$ is

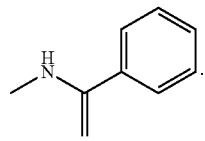

20. The method of claim 1 wherein $R_1$ is $H_3CO-$; $R_2$ is

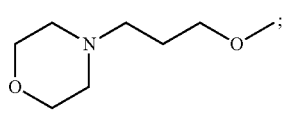

and $R_3$ is

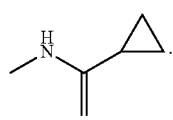

21. The method of claim 1 wherein $R_1$ is $H_3CO-$; $R_2$ is

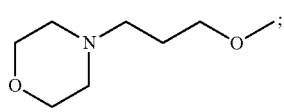

and $R_3$ is

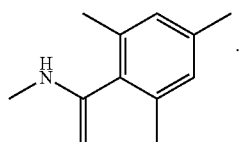

22. The method of claim 1 wherein $R_1$ is $H_3CO-$; $R_2$ is

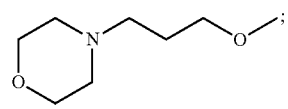

and $R_3$ is

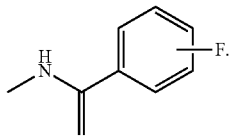

23. The method of claim 1 wherein $R_1$ is

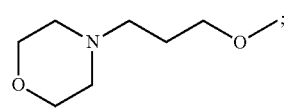

$R_2$ is $H_3CO-$; and $R_3$ is

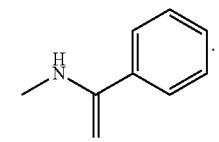

24. The method of claim 1 wherein $R_1$ is H; $R_2$ is H; and $R_3$ is

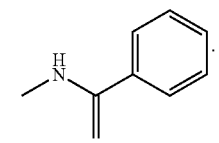

* * * * *

UNITED STATES PATENT AND TRADEMARK OFFICE
CERTIFICATE OF CORRECTION

PATENT NO. : 8,658,655 B2
APPLICATION NO. : 13/429755
DATED : February 25, 2014
INVENTOR(S) : Jeffrey R. Peterson, Haiching Ma and Sean Deacon It is certified that error appears in the above-identified patent and that said Letters Patent is hereby corrected as shown below:

In the Claims

Claim 19:

Column 27, lines 5-19, should read

19. The method of claim 1 wherein $R_1$ is $H_3CO$-; $R_2$ is

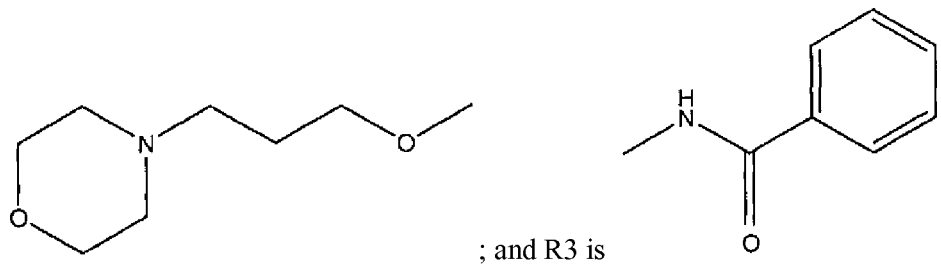

; and R3 is

Claim 20:

Column 27, lines 20-32, should read

20. The method of claim 1 wherein $R_1$ is $H_3CO$-; $R_2$ is

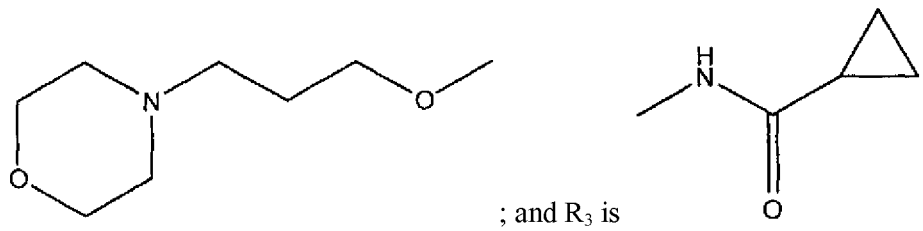

; and $R_3$ is

Signed and Sealed this
First Day of July, 2014

Michelle K. Lee
*Deputy Director of the United States Patent and Trademark Office*

CERTIFICATE OF CORRECTION (continued)
U.S. Pat. No. 8,658,655 B2

Claim 21:

Column 27, lines 35-45, should read

21. The method of claim 1 wherein $R_1$ is $H_3CO-$; $R_2$ is

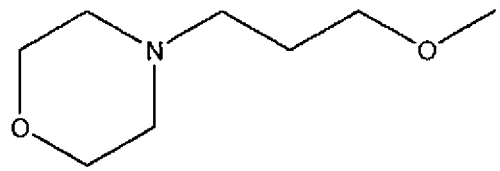 ; and $R_3$ is 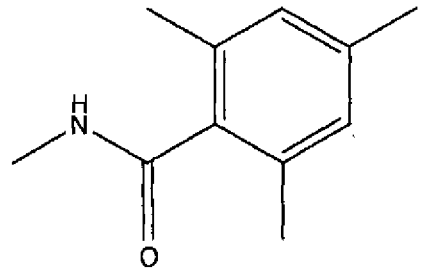

Claim 22:

Column 28, lines 5-17, should read

22. The method of claim 1 wherein $R_1$ is $H_3CO-$; $R_2$ is

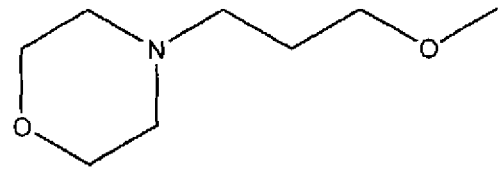 ; and $R_3$ is 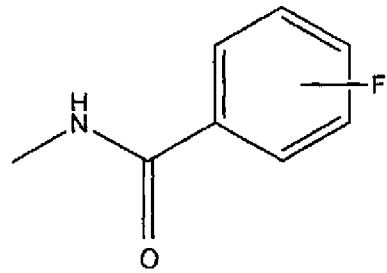

Claim 23:

Column 28, lines 20-35, should read

23. The method of claim 1 wherein $R_1$ is

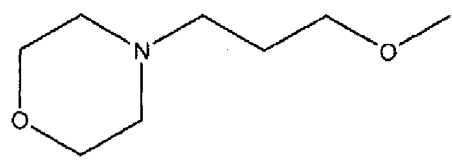 ; $R_2$ is $H_3CO-$; and $R_3$ is 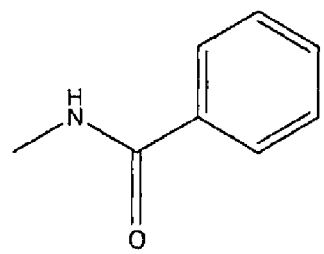

CERTIFICATE OF CORRECTION (continued)

Claim 24:

Column 28, lines 40-45, should read

24. The method of claim 1 wherein $R_1$ is H; $R_2$ is H; and $R_3$ is